(12) United States Patent
Bernhardt et al.

(10) Patent No.: US 6,391,657 B1
(45) Date of Patent: *May 21, 2002

(54) REMOVAL OF VIRUSES FROM PROTEIN SOLUTIONS BY ULTRAFILTRATION

(75) Inventors: Dieter Bernhardt, Cölbe; Albrecht Gröner, Seeheim; Thomas Nowak, Staufenberg-Mainzlas, all of (DE)

(73) Assignee: Aventis Behring GmbH, Marburg (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/598,264

(22) Filed: Feb. 7, 1996

(30) Foreign Application Priority Data

Feb. 9, 1995 (DE) .......................... 195 04 211

(51) Int. Cl.⁷ ...................... G01N 33/537; B01D 61/14
(52) U.S. Cl. .......................... 436/538; 436/536; 435/5; 210/651; 604/5.02
(58) Field of Search ................ 436/536, 538; 435/5; 210/649, 651; 604/5.02

(56) References Cited

U.S. PATENT DOCUMENTS

| | | | | |
|---|---|---|---|---|
| 4,576,928 A | * | 3/1986 | Tani et al. | 502/404 |
| 4,692,411 A | * | 9/1987 | Ghose | 435/243 |
| 4,857,196 A | * | 8/1989 | Manabe et al. | 210/500.3 |
| 5,017,292 A | * | 5/1991 | DiLeo et al. | 210/645 |
| 5,061,237 A | * | 10/1991 | Gessler et al. | 604/5 |

FOREIGN PATENT DOCUMENTS

DE  4113255  * 10/1991

OTHER PUBLICATIONS

Anthony J. DiLeo et al., "Size Exclusion Removal of Model Mammalian Viruses Using a Unique Membrane System, Part I: Membrane Qualification," Biologicals 21: 275–286 (1993).

Anthony J. DiLeo et al., "Size Exclusion Removal of Model Mammalian Viruses Using a Unique Membrane System, Part II: Module Qualification and Process Simulation," Biologicals 21: 287–296 (1993).

M. Burnouf–Radosevich et al, "Nanofiltration, a New Specific Virus Elimination Method Applied to High–Purity Factor IX and XI Concentrates," Vox Sang 67: 132–138 (1994).

D. Bernhardt et al., "Kreuzreaktive Antikörper bei Parvoviren," Tierärztl. Umschau 49: 481–483 (1994).

M. J. Cardosa et al., "Dot enzyme immunoassay: an alternative diagnostic aid for dengue fever and dengue haemorrhagic fever," Bulletin of the World Health Organization, 69(6): 741–745 (1991).

Webster's Ninth New Collegiate Dictionary, Merriam–Webster, Springfield, MA, 1990, p. 64 and page 252.*

* cited by examiner

*Primary Examiner*—Donna C. Wortman
(74) *Attorney, Agent, or Firm*—Finnegan, Henderson, Farabow, Garrett & Dunner, L.L.P.

(57) ABSTRACT

The invention relates to the removal of viruses from aqueous solutions, as a rule protein solutions, by ultrafiltration. This entails the viruses to be removed being increased in size by incubation with a high molecular weight receptor binding thereto, preferably a specific antibody, so that, on the one hand, the separation effect is improved and, on the other hand, a larger pore diameter which can now be chosen for the filters used also makes it possible for smaller viruses to be separated from larger protein molecules present in protein solutions, and, where appropriate, the filtration rate is increased.

15 Claims, No Drawings

REMOVAL OF VIRUSES FROM PROTEIN SOLUTIONS BY ULTRAFILTRATION

The invention relates to the removal of viruses from aqueous solutions, as a rule protein solutions, by ultrafiltration. This entails the viruses to be removed being increased in size by incubation with high molecular weight ligands binding thereto, preferably specific antibodies, so that, on the one hand, the separation effect is improved and, on the other hand, a larger pore diameter which can now be chosen for the filters used also makes it possible for smaller viruses to be separated from larger protein molecules present in protein solutions, and, where appropriate, the filtration rate is increased.

Proteins purified and concentrated from human plasma are used for therapy and prophylaxis of human diseases. These products are prepared from plasma pools consisting of about 10,000 individual donations. Since some of these donations may potentially be contaminated with human pathogenic viruses such as HIV-1/2, hepatitis B virus, hepatitis C virus and other viruses, there is the possibility of infection being caused by administration of the plasma proteins. In order to minimize this contamination hazard, donations are obtained only from healthy donors who are additionally tested for infection markers (antibodies against HIV 1 and HIV 2, HBsAg, antibodies against HCV and elevated liver function test results (ALT)); positive donations are rejected and not used for obtaining plasma proteins. The purification and concentration steps used in the industrial preparation of plasma proteins and, in particular, steps specifically introduced into the production to eliminate and/or inactivate viruses lead to plasma proteins with a very high safety standard.

In order to increase the safety of plasma proteins even further, there have been investigations of the use of filtration methods, for example dead-end and tangential flow filtration, in order to eliminate any viruses present in the protein solution. Filter units for eliminating viruses are produced by various companies (DiLeo, A. J. et al. Biologicals 21, 275–286 (1993); DiLeo A. J. et al. Biologicals 21, 287–296 (1993); Burnout, T. et al., Vox Sang. 67, 132–138 (1994)). Thus, for example, Asahi Chemical Industry Co. Ltd., Tokyo, Japan, produces filter units stating a defined (average) pore size, while, for example, Millipore Corp., Bedford, Mass., USA, produces filter units stating a nominal molecular weight cut off.

It has emerged from our investigations that viruses are held back at different rates by filters with different pore sizes, depending on the diameter of said viruses (HIV: 80–100 nm: HCV: 40–60 nm; HBV: 40–45 nm; picornaviruses: 24–30 nm; parvoviruses: 18–25 nm): (I) filters with an average pore diameter of 75 nm essentially retain HIV, while the other specified viruses are found in the filtrate; (II) filters with an average pore diameter of 35 nm retain HIV completely and HCV and HBV to a large extent, while, for example, picornaviruses and parvoviruses are found in the filtrate; (III) filters with an average pore diameter of 15 nm retain HIV, HCV and HBV and, to a large extent, for example picornaviruses and parvoviruses. Filtration through a filter with an average pore diameter of 15 nm leads to a general increase in the virus safety of plasma proteins. However, since most plasma proteins have such a high molecular weight that they cannot be filtered through a 15 nm filter, i.e. are likewise held back, only filters with an average pore diameter of 35 nm (or a nominal molecular weight cut off of 70,000 D to 100,000 D) are suitable for filtering most plasma proteins, but these do not remove to an adequate extent at least picornaviruses (such as, for example, hepatitis A virus) and parvoviruses (such as the human pathogenic parvovirus B 19) from plasma proteins.

The object therefore was to achieve an adequate, i.e. complete, retention even of small viruses by filtration, and to make filtration methods also applicable to those proteins which resemble simply in terms of their size a small virus. In addition, it was intended to increase the filtration rate as far as possible.

The object is achieved by the present invention in that the viruses to be removed are increased in size by binding to high molecular weight ligands, preferably specific antibodies, particularly preferably monoclonal antibodies, in principle of all subclasses, but preferably subclass IgG or IgM or parts thereof still capable of binding, which are, where appropriate, modified or enlarged by genetic engineering, to such an extent that they can be held back by filtration. The increase in size can also be achieved by aggregate formation. It is in fact possible with this method to separate relatively large proteins such as factor VIII or von Willebrand factor from such viruses of increased size by filtration, it now being possible to choose the pore size such that the proteins pass through and the viruses of increased size are held back. It is moreover possible by choice of a larger pore width, which is now possible, to increase the filtration rate. In the most general form, the present invention makes it possible to increase the size of any constituents of an aqueous solution by binding to high molecular weight ligands to such an extent that separation is then possible from the now smaller constituents in a filtration step.

Further examples of ligands which can be used for the purpose of the present invention for specific viruses are listed below:

| Ligand | Virus |
|---|---|
| Antibodies, possibly modified | HIV |
| CD4 receptor | HIV |
| Sialic acid (=derivatives, for example sialooligosaccharides) | Influenzaviruses |
| Heparan sulfate | HSV |
| C3d complement receptor/complement receptor 2 (CR2) | EBV |
| Acetyicholine receptor | Rabiesviruses |
| ICAM-1 (intracellular adhesion molecule-1) | Rhinoviruses |
| Gangliosides | Paramyxoviruses |
| IgA receptor | HBV |
| Epidermal Growth Factor Receptor | Vaccinia |
| Beta adrenergic receptor | Reovirus Serotype 3 |
| Immunoglobulins superfamily protein | Poliovirus |
| H-2 antigens | Semliki Forest Virus |

Human pathogenic viruses such as, for example, HBV, HCV, HIV, picornaviruses and parvoviruses may, despite selection of donors, be present in a plasma pool. These viruses bind to antibodies present in the protein solution, in particular either to antibodies present in the plasma pool during incubation of the low-cryo plasma or of the resuspended cryoprecipitate at 2° C. to 37° C. for 15 minutes to 36 hours, preferably at 2° C. to 8° C. for a period of 2 to 36 hours, in particular 4 to 18 hours, or at 10° C. to 25° C. for a period of 15 minutes to 18 hours, preferably 30 minutes to 6 hours, or to antibodies specifically added shortly before the filtration to the plasma protein solution to be filtered, which antibodies can be used in native form or a form modified chemically or by genetic engineering (for example low-cryo plasma, immunoglobulin fractions, purified immunoglobulins of human or animal origin, monoclonal antibodies)

during incubation of the protein solution at 2° C. to 37° C. for 15 minutes to 36 hours, preferably at 2° C. to 8° C. for a period of 2 to 36 hours, in particular 4 to 18 hours, or at 10° C. to 30° C. for a period of 15 minutes to 8 hours, preferably 30 minutes to 4 hours. The virus-antibody complexes formed in this way can be removed from the plasma protein solution by filtration, for example dead-end filtration or, preferably, tangential flow filtration.

EXAMPLE 1

Bovine parvovirus (BPV; ATCC VR-767), as model virus for the human pathogenic parvovirus B 19, was grown in diploid fetal bovine lung cells in EME medium containing 5% FCS and then separated from cells and cell debris by low-speed centrifugation (2000 g, 15 minutes, 4° C.); the virus-containing supernatant was divided into aliquots and stored at −70° C. until investigated. Porcine parvovirus (PPV; ATCC VR-742) was investigated for comparison; PPV was grown and isolated like BPV but in a permanent porcine kidney cell line (IB-RS-2 D10; ATCC CRL 1835).

The following test mixtures were mixed, incubated at 20° C. for 1 hour and then filtered through BMM process filter PLANOVA™ 35 (from Asahi Chemical Industry Co. Ltd., Tokyo, Japan) in accordance with the instructions of the manufacturing company. The infectiosity titer ($CCID_{50}$: cell culture infectious dose 50%) was determined in the starting material and in the filtrate after filtration.

| | Test A | Test B | Test C | Test D | Test E |
|---|---|---|---|---|---|
| Protein solution (260 ml) | Albumin (5%) | Albumin (5%) | Albumin (5%) | Albumin (5%) | Albumin (5%) |
| Virus material (30 ml) | BPV | BPV | BPV | PPV | PPV |
| Antibody-containing solution (30 ml) | PBS (no antibodies) | Human serum (B19-positive/ ELISA) | Human serum (B19-negative/ ELISA) | Human serum (B19-positive/ ELISA) | Human serum (B19-negative/ ELISA) |
| Infection titer before filtration ($CCID_{50}$) | $10^{5.2}$ | $10^{4.2}$ | $10^{5.1}$ | $10^{6.4}$ | $10^{6.2}$ |
| Infection titer after filtration ($CCID_{50}$) | $10^{4.9}$ | $10^{0.5}$ | $10^{4.3}$ | $10^{6.0}$ | $10^{5.9}$ |

Since BPV cross-reacts serologically with B19 (Bernhardt, D. et al., Tierärztl. Umschau 49, 481–483 (1994)), antibodies against B19 from human plasma also bind to BPV but not to PPV. The antigen-antibody complexes produced during the incubation are so large that, in contrast to uncompleted antigen, they cannot be filtered.

EXAMPLE 2

A licensed poliovirus vaccine for oral immunization (Oral-Virelon®; live attenuated vaccine) was suspended in a protein solution comprising 10% fetal calf serum in DMEM; purified immunoglobulin (Beriglobin®) was added to part of this virus suspension, and the same volume of PBS was added to the other part. After incubation at 15° C. for 2 hours, the samples were filtered (Sartocon®-Micro, 100,000 D nominal molecular weight cut off). Since the immunoglobulins neutralize polioviruses, so that an infectiosity assay in this part of the test provides no information about a reduction in concentration by the filtration, virus in samples of the retentates and of the filtrates was, after a pH shift (pH 4, 10 minutes; then centrifugation through a sucrose cushion of 25% (w/w) sucrose at 20,000 g, 45 minutes, 4° C. and resuspension of the pellet in PBS pH 7.2), detected in a dot-blot on nitrocellulose. The resuspended samples were initially diluted 1:2 in tris/glycine buffer pH 8.3 and then further diluted in a 1:3 dilution series; 100 μl portions of each dilution were applied to a nitrocellulose filter (pore size 0.4 μm), the membrane was blocked with skimmed milk powder (3%), incubated with antiserum against polioviruses (from rabbit) at 37° C. for 1 hour and then incubated further with POD-labeled anti-rabbit antibodies. The bound antibodies were visualized with 4-chloro-1-naphthol/$H_2O_2$ (dot-blot procedure as described by Cardosa, M J & Tio, P. H., Bull. WHO, 69, 741–745, 1991).

| | Test A | Test B |
|---|---|---|
| Protein solution (260 ml) | 10% of FCS in DMEM | 10% of FCS in DMEN |
| Virus material (30 ml) | Poliovirus | Poliovirus |
| Antibody-containing solution (30 ml) | purified immunoglobulins (Beriglobin) | PBS |
| Dot blot titer before filtration | 1024 | 1024 |
| Dot blot titer after after filtration | <2 | 256 |

The poliovirus-antibody complexes cannot, in contrast to uncomplexed antigens, be filtered; removal from the protein solution can therefore be achieved by adding immunoglobulins.

What is claimed is:

1. A process for removing unwanted substances from a liquid substance mixture comprising:
   binding one of said unwanted substances to a ligand to form a complex to increase the size of one of said unwanted substances,
   filtering the liquid substance mixture through a filter having an average pore diameter sufficient to filter out said complex of unwanted substance and ligand, and
   recovering the resulting filtrate,
   wherein the ligand is chosen from a CD4 receptor, a sialic acid or a derivative thereof, a heparin sulfate, a C3d complement receptor, an acetylcholine receptor, ICAM-1, a ganglioside, an IgA receptor, an epidermal growth factor receptor, a β-adrenergic receptor, an H-2 antigen, and an immunoglobulin superfamily protein.

2. The process according to claim 1, wherein the ligand is an immunoglobulin superfamily protein wherein the immunoglobulin superfamily protein is an antibody or a portion thereof and wherein said antibody or portion thereof has been modified chemically or through genetic engineering.

3. The process according to claim 2, wherein the antibody comprises an IgG or IgM antibody or portion thereof.

4. The process according to claim 2, wherein the antibody or a portion thereof is a monoclonal antibody or a portion thereof.

5. A process for removing unwanted substances from a liquid substance mixture comprising:
   binding one of said unwanted substances to a ligand to form a complex to increase the size of one of said unwanted substances, filtering the liquid substance mixture through a filter having an average pore diameter sufficient to filter out said complex of unwanted substance and ligand, and recovering the resulting filtrate, wherein the ligand is a monoclonal antibody or a portion thereof which has been modified chemically or through genetic engineering.

6. A process for removing viruses from a protein solution comprising:

binding one of said viruses to a ligand to form a complex to increase the size of one of said viruses, filtering the protein solution through a filter having an average pore diameter sufficient to filter out said complex of virus and ligand, and recovering the resulting filtrate, wherein the ligand is chosen from a CD4 receptor, a sialic acid or a derivative thereof, a heparin sulfate, a C3d complement receptor, an acetylcholine receptor, ICAM-1, a ganglioside, an IgA receptor, an epidermal growth factor receptor, a β-adrenergic receptor, an H-2 antigen, and an immunoglobulin superfamily protein.

7. The process according to claim 6, wherein the viruses are chosen from HBV, HCV, HIV, picornavirus, parvovirus, influenza, HSV, EBV, rabies virus, rhinovirus, vaccinia, paramyxovirus, reovirus serotype 3, polio virus, semliki forest virus, and hepatitis A virus.

8. The process according to claim 6, wherein the protein solution is incubated to permit virus/ligand binding before the filtering step.

9. The process according to claim 8, wherein the incubation is performed at 2° C. to 37° C. for 15 minutes to 36 hours.

10. The process according to claim 9, wherein the incubation is performed for 4 to 18 hours.

11. The process according to claim 9, wherein the incubation is performed at 10° C. to 25° C. for 15 minutes to 18 hours.

12. The process according to claim 9, wherein the incubation is performed for 30 minutes to 6 hours.

13. The process according to claim 6, wherein the filtering is performed using a hollow fiber filter or a membrane filter.

14. The process according to claim 6, wherein the filtering is performed using a tangential flow method.

15. A process for removing viruses from a protein solution comprising;

binding one of said viruses to a ligand to form a complex to increase the size of one of said viruses, filtering the protein solution through a filter having an average pore diameter sufficient to filter out said complex of virus and ligand, and recovering the resulting filtrate, wherein the ligand is a monoclonal antibody or a portion thereof which has been modified chemically or through genetic engineering.

* * * * *